United States Patent [19]
Kim et al.

[11] Patent Number: 5,989,878
[45] Date of Patent: Nov. 23, 1999

[54] FERMENTATION PROCESS FOR PREPARING ERYTHRITOL USING MUTANT CELLS BY CONTROLLING OSMOTIC PRESSURE

[75] Inventors: Sang Yong Kim, Kyonggi; Deok Kun Oh, Chonbuk; Soo Ryun Jung, Seoul, all of Rep. of Korea

[73] Assignee: Bolak Co., Ltd., Kyunggi-do, Rep. of Korea

[21] Appl. No.: 09/021,304

[22] Filed: Feb. 10, 1998

[30] Foreign Application Priority Data

Dec. 30, 1997 [KR] Rep. of Korea ............... 97-78786

[51] Int. Cl.⁶ .......................................... C12P 7/18
[52] U.S. Cl. ............................ 435/158; 435/911
[58] Field of Search .................... 435/158, 911

[56] References Cited

U.S. PATENT DOCUMENTS

| | | | |
|---|---|---|---|
| 4,906,569 | 3/1990 | Maeda et al. | 435/158 |
| 4,923,812 | 5/1990 | Horikita et al. | 435/158 |
| 4,939,091 | 7/1990 | Sasaki et al. | 435/158 |
| 5,902,739 | 5/1999 | Abe et al. | 435/158 |

OTHER PUBLICATIONS

Aoki et al., *Biotechnology Letters*, 15:4, pp. 383–388, Apr. 1993.
Ishizuka et al., *Journal of Fermentation and Bioengineering*, 68:5, pp. 310–314, 1989.
Hajny et al., *Applied Microbiology*, 12:2, pp. 240–246, May 1964.

*Primary Examiner*—Herbert J. Lilling
*Attorney, Agent, or Firm*—Kenyon & Kenyon

[57] ABSTRACT

The present invention relates to a fermentation process for preparing erythritol with high productivity with novel mutant of *Trigonopsis variabilis*, more specifically, for preparing erythritol under optimal fermentation conditions for maximum erythritol production by optimizing the environmental conditions of culture such as pH, temperature and controlling osmotic pressure. A two-stage fermentation was performed to control osmotic pressure. Osmotic pressure was adjusted to a low level during growth phase and to a high level during production phase by adding glucose and NaCl. Therefore, erythritol production could be increased due to the increased mutant cells.

3 Claims, No Drawings

5,989,878

FERMENTATION PROCESS FOR PREPARING ERYTHRITOL USING MUTANT CELLS BY CONTROLLING OSMOTIC PRESSURE

BACKGROUND OF THE INVENTION

1. Field of the Invention

The present invention relates to a fermentation process for preparing erythritol with high productivity using novel mutant of *Trigonopsis variabilis*, more specifically, for preparing erythritol under optimal fermentation conditions for maximum erythritol production by optimizing the environmental conditions of culture such as pH and temperature, and controlling osmotic pressure using a two stage fermentation, in which osmotic pressure was adjusted to be a low level during growth phase, and to be a high level during production phase.

2. Description of Prior Art

Erythritol, a four carbon sugar alcohol, is a naturally occurring substance and is widely distributed in nature. Like most of the other polyols, it is a metabolite or storage compound for seaweeds and mushrooms. Fruits like melons, grapes and pears also contain erythritol. As it is often produced by bacteria, fungi, and yeasts, erythritol also occurs frequently in fermented food systems like wines or beers, and processed vegetables such as soy sauce and the oriental miso bean paste.

Erythritol is a moderately sweet bulking agent with 60~70 percent of the sweetness of sucrose in a 10 percent solution. Its high negative heat of solution provides the crystalline material with a strong cooling effect. As it has a taste which is very close to sucrose and with no bitter aftertaste, it is ideal to improve the taste by combination with intense sweeteners like aspartame.

Being a small molecule, erythritol has strong colligative properties, i.e. a strong freezing point depression and a boiling point elevation effect as well as a high osmotic pressure. In combination with its low hygroscopicity and viscosity in solution, it is very useful to reduce and control the water activity of foodstuffs.

Erythritol production from natural sources such as fruits and vegetables is not practical due to their relative small amounts. Erythritol can be chemically produced by reduction of meso-tartarate, oxidation and reduction of 4,6-o-ethylidene-D-glucose, hydrolysis of dealdehyde starch, or hydrogenation process. Since erythritol production by the chemical methods has been found to be expensive, it is worthwhile to explore an alternative method for the effective production of erythritol using microorganisms.

Erythritol can be produced by microbial methods with the osmophilic yeasts, especially species of the genus Torulopsis, such as *T magnoliae, T. veratilis,* and *T. candida; Endomycopsis chodati; Hansenula supelliculsa; Pichia miso; Monilliella tomentosa* var. *pollinis; Trigonopsis variabilis*; Trichosporonoides; *Candida zeylanoides;* and Aureobasidium. Some bacteria such as *Leuconostoc oenos* can also produce erythritol. *Monilliella tomentosa* var. *pollinis* produced erythritol on a medium containing 35.7% glucose with 45.6% yield.

Erythritol production using this strain has not been applied to industrial scale due to the formation of by-products such as glycerol and ribitol. Industrial production of erythritol has been performed by the mutant of Aureobasidiumn. The mutant was isolated and developed by cooperative study of Nikken Chemical and National Food Research Institute of Japan. The mutant produced erythritol with 47.6% yield on a medium containing 22.5% glucose and 2 g/L-h volumetric productivity.

It was found that most of polyols producing strains can grow under the conditions of high osmotic pressure such as the high concentration of sugars and salts. This fact suggests that polyols production has the relation to osmotic pressure. Reed et al. reported that glycerol productivity was improved by culturing a glycerol producing strain under the conditions of high osmotic pressure. However, erythritol production by controlling osmotic pressure has not been reported.

Therefore, in this invention, a wild strain of *Trigonopsis variabilis* KCCM 35523 without producing by-products was selected to produce erythritol. The wild strain was mutated with NTG(N-methyl-N'-nitro-N-nitroguanidine) treatment. One of mutants has superior properties in erythritol yield from glucose, volumetric productivity, and sugar tolerance compared to the wild strain. By using the mutant of *T. variabilis*, the effect of osmotic pressure on erythritol production was investigated, and two-stage fermentation in which osmotic pressure was adjusted to be a low level during growth phase and to be a high level during production phase was performed in order to increase erythritol production.

SUMMARY OF THE INVENTION

The object of the present invention is to provide novel mutants cells of *Trigonopsis variabilis*, which were deposited to Korean Culture Center of Microorganism Department of Food Engineering, College of Engineering, Yonsei University, Sodaemun-gu, Seoul 120-749, Korea, with accession number KCCM-10120 on Dec. 22, 1997 under Budapest treaty, for preparing erythritol with high productivity.

The other object of the present invention is to provide the optimal fermentation conditions for maximum production of erythritol using mutant cells by controlling following conditions;

i) fermenting glucose medium with mutant cells wherein
  a) concentration of mutant cells by controlling osmotic pressure during fermentation process is 15~35 g/L;
  b) composition of medium for maximum production of erythritol consists of 10~50 (w/v)% glucose, 0.2~2.0 (w/v)% yeast extract, 0~5 (w/v)% NaCl, 0~5 (w/v)% KCl;
  c) pH of culture medium is 4.5~5.5;
  d) temperature of cultivation is 27~33° C.;
  e) aeration rate of the medium is 0.5~2.0 volume of air per volume of medium per minute; and
  f) agitation speed of the medium is 300~1200 rpm;
ii) removing the mutant cells and other residue from the fermentation medium; and
iii) separating and recovering erythritol from the fermentation medium of step (ii).

The further object of the present invention is to provide a fermentation process wherein the mutant cells used for fermentation are prepared by cultivating frozen *Trigonopsis variabilis* (accession number KCCM-10120) in YM medium (0.8~1.2 (w/v)% glucose, 0.4~0.6 (w/v)% peptone, 0.2~0.4 (w/v)% yeast extract, 0.2~0.4 (w/v)% malt extract) at 27~33° C. for 20~28 hours.

The further object of the present invention is to provide a fermentation process wherein the osmotic pressure is controlled by i) the osmotic pressure is 0.2~0.8 Osm/kg during growth phase and 1.2~1.8 Osm/kg during erythritol production phase; and ii) 10~20% glucose, 0~5% NaCl, and 0~5% KCl are intermittently fed into the culture broth during erythritol production phase to maintain a high osmotic pressure for the effective production of erythritol.

DETAILED DESCRIPTION OF THE INVENTION

The present invention concerns a method of obtaining erythritol with a high yield and a high volumetric productivity in *Trigonopsis variabilis* mutant by controlling osmotic pressure.

The mutant cells used for the present invention are isolated by following method. *T variabilis* KCCM 35523 is incubated at 28~32° C. for 24 h on the fermentation agar plate containing 20% glucose. A single colony is incubated in a 250-mL flask containing 50 mL of YM(yeast-malt) broth. It is incubated at 28~32° C. and 220~260 rpm until the optical density of culture broth at 600 nm reaches at 1.0. The grown cells are collected by centrifugation at 3000 g for 20 min and washed with 0.1 M citrate buffer pH 5.5. The collected cells are resuspended in the buffer solution containing 0.01% NTG and incubated at 28~32° C. for 25~35 min. After NTG treatment, the cells are incubated at 28~32° C. for 8~12 h in YM broth and plated on the agar plate containing 40% glucose and 0.5% yeast extract for the selection of a high erythritol producing mutant. Single colonies are selected as fast growing mutants. The selected colonies are transferred on the fermentation medium containing 20% glucose to test erythritol producing activity in shake flask. After incubating at 28~32° C. and 220~260 rpm in 100~140 h, a high erythritol producing mutant is selected and colony produced is separated by repeating separation method more than 3 times. The obtained colony is again spread and cultured to YM medium under UV illumination of 250~270 nm. Finally, growing colony is isolated and obtained as mutant cells and used as a producing strain in this invention. These mutant cells were deposited to Korean Culture Center of Microorganism with accession number KCCM-10120.

The following is fermentation method for producing erythritol using mutants cells.

Seed Culture

A frozen (−70° C.) mutant cells of *Trigonopsis variabilis* (KCCM-10120) are cultivated in a 250-mL flask containing 40~60 mL growth medium (0.8~1.2 (w/v)% glucose, 0.4~0.6 (w/v)% peptone, 0.3~0.5 (w/v)% yeast extract and 0.2~0.4 (w/v)% malt extract) at 28~32° C. in 220~260 rpm for 20~28 h, and this seed culture is transferred to a 250-ml flask or a 5-L fermentor for producing erythritol in main culture.

Main Culture

Flask experiments with fermentation medium are performed at 28~32° C. and 220~260 rpm in 100~140 h. The fermentation medium consists of glucose as carbon source and yeast extract as nitrogen source. For the experimental purpose, glucose concentration is adjusted. Batch and fed-batch culture in the fermentor are performed at 30° C. in pH 5.5 during the fermentation. Aeration rate is in the range of 1.0~2.0 vvm. Agitation speed is gradually increased from 300 to 1,200 rpm to maintain the level of dissolved oxygen above 20%. Working volume in batch culture is 3 L. Fed-batch culture is performed with initial medium of 2 L, and finial volume is 3 L by adding twice 500 mL of feeding medium at 30 h and 55 h. The initial medium consists of 150~250 g glucose and 5~15 g yeast extract, and the feeding medium contains 550~650 g glucose and 50~60 g NaCl. After feeding medium at 25~35 h and 50~60 h, Osmolarity of culture broth are 1.6~1.8 and 1.5~1.7 Osm/kg, respectively.

The fermentation process is preferably by fed-batch process. After glucose is completely consumed in the medium, the amount of erythritol is measured by high performance liquid chromatography equipped with Carbohydrate Analysis column. Dry cell weight is estimated by using a calibration curve made from relationship between optical density at 600 nm and dry cell weight. Glucose is measured by dinitrosalicylic acid method. Osmotic pressure is determined by automatic semi-micro osmometer. The specific growth rate is determined by the slope from the plotting for time(x) and logarithmic cell mass(Y), and the specific production rate of erythritol is determined by dividing cell mass over the slope of erythritol production against time using polynomial regression.

The measured yield of erythritol is 35~55% of glucose consumption and volumetric productivity is 1.7~2.5 g/L-hr, which are increased by 2~4 fold compared with conventional fermentation yield and productivity.

Finally the fermentation medium is centrifuged for removing cells and other residue, and the supernatant is filtered and dialyzed for obtaining erythritol.

The present invention can be explained more specifically by following examples.

EXAMPLE I

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250-ml flask containing fermentation medium, which consisted of 10~40% glucose and 0.4~0.6% yeast extract, for producing erythritol in main culture. Flask experiments with fermentation medium were performed at 28~32° C. and 220~260 rpm in 140~340 h.

After 70 hours fermentation, the amount of erythritol from 10% glucose (Osmolarity=0.52 Osm/kg) is measured by HPLC equipped with Carbohydrate Analysis column. The obtained erythritol is 30 g/L and volumetric productivity is 0.43 g/L-hr.

After 144 hours fermentation, the amount of erythritol from 20% glucose (Osmolarity=0.99 Osm/kg) is measured by HPLC equipped with Carbohydrate Analysis column. The obtained erythritol is 73 g/L and volumetric productivity is 0.51 g/L-hr.

After 240 hours fermentation, the amount of erythritol from 30% glucose (Osmolarity=1.56 Osm/kg) is measured by HPLC equipped with Carbohydrate Analysis column. The obtained erythritol is 80 g/L volumetric productivity is 0.33 g/L-hr, and residual glucose is 10.8%.

Comparative Example

The frozen (−70° C.) wild cells of *Trigonopsis variabilis* (KCCM-35523) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250-ml flask containing fermentation medium, which consisted of 10~40% glucose and 0.4~0.6% yeast extract, for producing erythritol in main culture. Flask experiments with fermentation medium were performed at 28~32° C. and 220~260 rpm in 240 h.

After 240 hours fermentation, the amount of erythritol from 10% glucose (Osmolarity=0.52 Osm/kg) is measured by HPLC equipped with Carbohydrate Analysis column. The obtained erythritol is 15 g/L and volumetric productivity is 0.06 g/L-hr.

After 240 hours fermentation, the amount of erythritol from 20% glucose (Osmolarity=0.99 Osm/kg) is measured by HPLC equipped with Carbohydrate Analysis column. The obtained erythritol is 14 g/L, volumetric productivity is 0.06 g/L-hr, and residual glucose is 6.4%.

After 240 hours fermentation, the amount of erythritol from 30% glucose (Osmolarity=1.56 Osm/kg) is measured by HPLC equipped with Carbohydrate Analysis column. The obtained erythritol is 12 g/L volumetric productivity is 0.05 g/L-hr, and residual glucose is 24.2%.

EXAMPLE II

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250-ml flask containing fermentation medium, which consisted of 15% glucose, 0.0~0.7M NaCl and 0.4~0.6% yeast extract, for producing erythritol in main culture. Flask experiments with fermentation medium were performed at 28~32° C. and 220~260 rpm in 140~340 h.

After 120 hours fermentation, the amount of erythritol from 15% glucose and 0.0M KCl (Osmolarity=0.79 Osm/kg) is measured by HPLC equipped with Carbohydrate Analysis column. The obtained erythritol is 50 g/L and volumetric productivity is 0.42 g/L-hr.

After 120 hours fermentation, the amount of erythritol from 15% glucose and 0.62M KCl (Osmolarity=1.66 Osm/kg) is measured by HPLC equipped with Carbohydrate Analysis column. The obtained erythritol is 66 g/L and volumetric productivity is 0.55 g/L-hr.

EXAMPLE III

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250 ml flask containing fermentation medium, which consisted of 15% glucose, 0.0~0.7M NaCl and 0.4~0.6% yeast extract, for producing erythritol in main culture. Flask experiments with fermentation medium were performed at 28~32° C. and 220~260 rpm in 140~340 h.

After 120 hours fermentation, the amount of erythritol from 15% glucose and 0.0M NaCl (Osmolarity=0.79 Osm/kg) is measured by HPLC equipped with Carbohydrate Analysis column. The obtained erythritol is 50 g/L and volumetric productivity is 0.42 g/L-hr.

After 120 hours fermentation, the amount of erythritol from 15% glucose and 0.61M NaCl (Osmolarity=1.64 Osm/kg) is measured by HPLC equipped with Carbohydrate Analysis column. The obtained erythritol is 65 g/L, volumetric productivity is 0.54 g/L-hr, and residual glucose is 0.7%.

EXAMPLE IV

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 20% glucose, and 0.4~0.6% yeast extract for producing erythritol in main culture. Fermentation is performed at 30° C. for 3 days and aeration rate is 1.0~2.0 vvm, agitation speed is 300~1200 rpm, and pH is 3.5~7.5.

After 72 hours fermentation, the amount of erythritol from 20% glucose and pH 3.5 is measured by HPLC equipped with Carbohydrate Analysis column. The obtained erythritol is 56 g/L, volumetric productivity is 0.78 g/L-hr, and residual glucose is 1.7%.

After 72 hours fermentation, the amount of erythritol from 20% glucose and pH 5.5 is measured by HPLC equipped with Carbohydrate Analysis column. The obtained erythritol is 77 g/L and volumetric productivity is 1.07 g/L-hr.

After 72 hours fermentation, the amount of erythritol from 20% glucose and pH 7.5 is measured by HPLC equipped with Carbohydrate Analysis column. The obtained erythritol is 58 g/L, volumetric productivity is 0.81 g/L-hr, and residual glucose is 0.8%.

EXAMPLE V

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 20% glucose, and 0.4~0.6% yeast extract for producing erythritol in main culture. Fermentation is performed at pH 5.5 for 3 days and aeration rate is 1.0~2.0 vvm, agitation speed is 300~1200 rpm, and temperature is 26~34° C.

After 72 hours fermentation, the amount of erythritol from 20% glucose and 26° C. is measured by HPLC equipped with Carbohydrate Analysis column. The obtained erythritol is 50 g/L, volumetric productivity is 0.69 g/L-hr, and residual glucose is 2.4%.

After 72 hours fermentation, the amount of erythritol from 20% glucose and 30° C. is measured by HPLC equipped with Carbohydrate Analysis column. The obtained erythritol is 77 g/L and volumetric productivity is 1.07 g/L-hr.

After 72 hours fermentation, the amount of erythritol from 20% glucose and 34° C. is measured by HPLC equipped with Carbohydrate Analysis column. The obtained erythritol is 54 g/L, volumetric productivity is 0.75 g/L-hr, and residual glucose is 1.3%.

EXAMPLE VI

The frozen (−70° C.) mutant cells of *Trigonopsis uaribilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C.; and 220~260 rpm. The seed cells are cultivated in a 250-ml flask containing fermentation medium, which consisted of 10~40% glucose and 0.4~0.6% yeast extract, for producing erythritol in main culture. Flask experiments with fermentation medium were performed at 28~32° C. and 220~260 rpm in 14 0~340 h.

Fermentation with 10% glucose (Osmolarity=0.52 Osm/kg) is performed. The obtained specific growth rate is 0.11 $h^{-1}$ and specific production rate of erythritol is 0.23 g/g-day.

Fermentation with 20% glucose (Osmolarity=0.99 Osm/kg) is performed. The obtained specific growth rate is 0.07 $h^{-1}$ and specific production rate of erythritol is 0.61 g/g-day.

Fermentation with 30% glucose (Osmolarity=1.56 Osm/kg) is performed. The obtained specific growth rate is 0.04 $h^{-1}$ and specific production rate of erythritol is 0.73 g/g-day.

EXAMPLE VII

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250-ml flask containing fermentation medium, which consisted of 15% glucose, 0.0~0.7M KCl and 0.4~0.6% yeast extract, for producing erythritol in main culture. Flask experiments with fermentation medium were performed at 28~32° C. and 220~260 rpm in 140~340 h.

Fermentation with 15% glucose and 0.0M KCl (Osmolarity=0.79 Osm/kg) is performed. The obtained specific growth rate is 0.08 $h^{-1}$ and specific production rate of erythritol is 0.42 g/g-day.

Fermentation with 15% glucose and 0.27M KCl (Osmolarity=1.07 Osm/kg) is performed. The obtained specific growth rate is 0.06 $h^{-1}$ and specific production rate of erythritol is 0.62 g/g-day.

Fermentation with 15% glucose and 0.62M NaCl (Osmolarity=1.66 Osm/kg) is performed. The obtained specific growth rate is 0.04 $h^{-1}$ and specific production rate of erythritol is 0.76 g/g-day.

EXAMPLE VIII

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 250 ml flask containing fermentation medium, which consisted of 15% glucose, 0.0~0.7M NaCl and 0.4~0.6% yeast extract, for producing erythritol in main culture. Flask experiments with fermentation medium were performed at 28~32° C. and 220~260 rpm in 140~340 h.

Fermentation with 15% glucose and 0.0M NaCl (Osmolarity=0.79 Osm/kg) is performed. The obtained specific growth rate is 0.08 $h^{-1}$ and specific production rate of erythritol is 0.42 g/g-day.

Fermentation with 15% glucose and 0.27M NaCl (Osmolarity=1.07 Osm/kg) is performed. The obtained specific growth rate is 0.06 $h^{-1}$ and specific production rate of erythritol is 0.62 g/g-day.

Fermentation with 15% glucose and 0.61M NaCl (Osmolarity=1.64 Osm/kg) is performed. The obtained specific growth rate is 0.03 $h^{-1}$ and specific production rate of erythritol is 0.85 g/g-day.

EXAMPLE IX

The frozen (−70° C.) mutant cells of *Trigonopsis variabilis* (KCCM-10120) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 40% glucose, and 0.4~0.6% yeast extract for producing erythritol in main culture. Batch fermentation is performed at 30° C. and aeration rate is 1.0~2.0 vvm, agitation speed is 300~1200 rpm, and pH is 5.5.

After 160 hours fermentation, the amount of erythritol from 40% glucose is measured by HPLC equipped with Carbohydrate Analysis column. The obtained erythritol is 140 g/L, volumetric productivity is 0.88 g/L-hr.

EXAMPLE X

The frozen (−70° C.) mutant cells of *Trigonopsis variabilis* (KCCM-10120) are cultivated in a 250-ml flask containing 50 ml growth medium (0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 40% glucose, and 0.4~0.6% yeast extract for producing erythritol in main culture. Fermentation is performed at 30° C. and aeration rate is 1.0~2.0 vvm, agitation speed is 300~1200 rpm, and pH is 5.5. Fed-batch culture was performed with initial medium of 2 L and finial volume was 3 L by adding twice 500 mL of feeding medium at 30 h and 55 h. The initial medium consisted of 200 g glucose and 10 g yeast extract and the feeding medium contained 500 g glucose and 55 g NaCl. After feeding medium at 30 h and 55 h, Osmolarity of culture broth were 1.68 and 1.60 Osm/kg, respectively.

After 80 hours fermentation, the amount of erythritol from 40% glucose is measured by HPLC equipped with Carbohydrate Analysis column. The obtained erythritol is 170 g/L, volumetric productivity is 2.13 g/L-hr.

We claim:

1. A fermentation method for maximum production of erythritol using a mutant of *Trigonopsis variabilis* deposited to Korean Culture Center of Microorganism with accession number KCCM-10120 comprising the step of:

i) fermenting glucose medium with mutant cells wherein
   a) concentration of mutant cells by controlling osmotic pressure during fermentation process is 15~35 g/L;
   b) composition of medium for maximum production of erythritol consists of 10~50 (w/v)% glucose, 0.2~2.0 (w/v)% yeast extract, 0~5 (w/v)% NaCl, 0~5 (w/v)% KCl;
   c) pH of culture medium is 4.5~5.5;
   d) temperature of cultivation is 27~33° C.;
   e) aeration rate of the medium is 0.5~2.0 volume of air per volume of medium per minute; and
   f) agitation speed of the medium is 300~1200 rpm;

ii) removing the mutant cells and other residue from the fermentation medium; and iii) separating and recovering erythritol from the fermentation medium of step (ii).

2. The fermentation process according to claim 1, wherein the mutant cells used for fermentation are prepared by cultivating frozen *Trigonopsis variabilis* (accession number KCCM-10120) in YM medium (0.8~1.2 (w/v)% glucose, 0.4~0.6 (w/v)% peptone, 0.2~0.4 (w/v)% yeast extract, 0.2~0.4 (w/v)% malt extract) at 27~33° C. for 20~28 hours.

3. The fermentation process according to claim 1, wherein the osmotic pressure is controlled by i) the osmotic pressure is 0.2~0.8 Osm/kg during growth phase and 1.2~1.8 Osm/kg during erythritol production phase; and ii) 10~20% glucose, 0~5% NaCl, and 0~5% KCl are intermittently fed into the culture broth during erythritol production phase to maintain a high osmotic pressure for the effective production of erythritol.

* * * * *